United States Patent [19]
Diamond et al.

[11] 4,150,154
[45] Apr. 17, 1979

[54] AMIDINOUREAS

[75] Inventors: Julius Diamond, Morris Plains, N.J.; Jerome J. Zalipsky, Melrose Park, Pa.

[73] Assignee: William H. Rorer, Inc., Fort Washington, Pa.

[21] Appl. No.: 554,379

[22] Filed: Mar. 3, 1975

[51] Int. Cl.$^2$ .................... A61K 31/17; C07C 127/00
[52] U.S. Cl. ............................... 424/322; 260/553 A
[58] Field of Search .................... 260/553 A; 424/322

[56] References Cited

U.S. PATENT DOCUMENTS 3,784,582   1/1974   Walls et al. ...................... 260/553 A Primary Examiner—Frederick E. Waddell
Attorney, Agent, or Firm—James A. Nicholson; John C. Smith, Jr.

[57] ABSTRACT

This invention describes novel chemical compounds which are 1-amidino-3-phenylureas. The method of preparing these compounds and their pharmaceutical uses is also disclosed.

37 Claims, No Drawings

AMIDINOUREAS

DESCRIPTION AND PREFERRED EMBODIMENTS

This invention describes a class of novel chemical compounds which comprises a urea moiety which is substituted in the 1-position by an amidino group and in the 3-position with a substituted phenyl ring thus forming 1-amidino-3-substitutedphenylureas. This invention also describes the non-toxic pharmaceutically acceptable salts; the method of preparing these compounds; and their pharmaceutical uses.

The novel compounds of this invention are described by the structural formula I

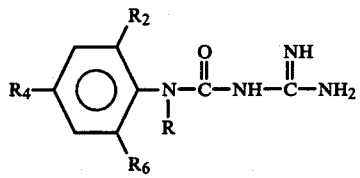

where:
R is hydrogen or loweralkyl;
$R_2$ is loweralkyl;
$R_4$ is loweralkyl, halo or loweralkoxy;
$R_6$ is hydrogen, loweralkyl, halo, haloloweralkyl, nitro, loweralkylsulfonyl or loweralkoxy; and the non-toxic acid addition salts thereof.

In the descriptive portions of this invention, the following definitions apply:

The term "loweralkyl" refers to a loweralkyl hydrocarbon group containing from 1 to about 6 carbon atoms which may be straight chained or branched.

The term "loweralkoxy" signifies an alkoxy group containing from 1 to about 6 carbon atoms which may be straight chained or branched.

Compounds of this invention which are preferred are described by the general formula I where:
R is hydrogen or loweralkyl;
$R_2$ is loweralkyl;
$R_4$ is loweralkyl or halo; and
$R_6$ is loweralkyl or halo.

The more preferred compounds of this invention include those compounds where:
R is hydrogen or methyl;
$R_2$ is methyl or ethyl;
$R_4$ is methyl, ethyl, propyl, i-propyl, butyl, chloro, bromo or fluoro; and
$R_6$ is methyl, ethyl, chloro, bromo or fluoro.

The most preferred compounds are those described where:
R is hydrogen or methyl;
$R_2$ is methyl or ethyl;
$R_4$ is methyl, ethyl, chloro, bromo or fluoro; and
$R_6$ is methyl, ethyl, chloro or bromo.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, higher molecular weight acids, etc., and include such as:

| | |
|---|---|
| hydrochloric acid | succinic acid, |
| hydrobromic acid, | glycolic acid, |
| sulfuric acid, | lactic acid, |
| nitric acid, | salicylic acid, |
| phosphoric acid, | benzoic acid, |
| methane sulfonic acid, | nicotinic acid, |
| benzene sulfonic acid, | phthalic acid, |
| acetic acid, | stearic acid, |
| porpionic acid, | oleic acid, |
| malic acid, | abietic acid, etc. |

Representative compounds of this invention which are particularly useful are as follows:

1-amidino-3-(2,4-dimethylphenyl)urea
1-amidino-3-(2-methyl-4-ethylphenyl)urea
1-amidino-3-(2-methyl-4-propylphenyl)urea
1-amidino-3-(2-methyl-4-i-propylphenyl)urea
1-amidino-3-(2-methyl-4-butylphenyl)urea
1-amidino-3-(2-methyl-4-chlorophenyl)urea
1-amidino-3-(2-methyl-4-bromophenyl)urea
1-amidino-3-(2-methyl-4-fluorophenyl)urea
1-amidino-3-(2-methyl-4-methoxyphenyl)urea
1-amidino-3-(2-methyl-4-ethoxyphenyl)urea
1-amidino-3-(2,4-diethylphenyl)urea
1-amidino-3-(2-ethyl-4-propylphenyl)urea
1-amidino-3-(2-ethyl-4-i-propylphenyl)urea
1-amidino-3-(2-ethyl-4-butylphenyl)urea
1-amidino-3-(2-ethyl-4-chlorophenyl)urea
1-amidino-3-(2-ethyl-4-bromophenyl)urea
1-amidino-3-(2-ethyl-4-fluorophenyl)urea
1-amidino-3-(2-ethyl-4-methoxyphenyl)urea
1-amidino-3-(2-ethyl-4-ethoxyphenyl)urea
1-amidino-3-(2-propyl-4-chlorophenyl)urea
1-amidino-3-(2-propyl-4-fluorophenyl)urea
1-amidino-3-(2-propyl-4-bromophenyl)urea
1-amidino-3-(2-propyl-4-methoxyphenyl)urea
1-amidino-3-(2-i-propyl-4-chlorophenyl)urea
1-amidino-3-(2-i-propyl-4-fluorophenyl)urea
1-amidino-3-(2-i-propyl-4-bromophenyl)urea
1-amidino-3-(2-i-propyl-4-methoxyphenyl)urea
1-amidino-3-(2-butyl-4-chlorophenyl)urea
1-amidino-3-(2-butyl-4-fluorophenyl)urea
1-amidino-3-(2-butyl-4-bromophenyl)urea
1-amidino-3-(2-butyl-4-methoxyphenyl)urea
1-amidino-3-(2,4,6-trimethylphenyl)urea
1-amidino-3-(2,4-dimethyl-6-ethylphenyl)urea
1-amidino-3-(2,4-dimethyl-6-chlorophenyl)urea
1-amidino-3-(2,4-dimethyl-6-bromophenyl)urea
1-amidino-3-(2,4-dimethyl-6-fluorophenyl)urea
1-amidino-3-(2-methyl-4-ethyl-6-chlorophenyl)urea
1-amidino-3-(2-methyl-4-ethyl-6-bromophenyl)urea
1-amidino-3-(2-methyl-4-ethyl-6-fluorophenyl)urea
1-amidino-3-(2,4-diethyl-6-chlorophenyl)urea
1-amidino-3-(2,4-diethyl-6-bromophenyl)urea
1-amidino-3-(2,4-diethyl-6-fluorophenyl)urea
1-amidino-3-(2-methyl-4,6-dichlorophenyl)urea
1amidino-3-(2-methyl-4-chloro-6-bromophenyl)urea
1-amidino-3-(2-methyl-4-chloro-6-fluorophenyl)urea
1-amidino-3-(2-methyl-4-bromo-6-chlorophenyl)urea
1-amidino-3(2-methyl-4-fluoro-6-chlorophenyl)urea
1-amidino-3-(2-methyl-4-bromo-6-fluorophenyl)urea
1-amidino-3-(2-methyl-4-fluoro-6-bromophenyl)urea
1-amidino-3-(2,6-dimethyl-4-methoxyphenyl)urea
1-amidino-3-(2,6-diethyl-4-methoxyphenyl)urea 1-amidino-3-(2-methyl-4-methoxy-6-chlorophenyl)urea
1-amidino-3-(2-methyl-4-ethoxy-6-chlorophenyl)urea The compounds of structure I are useful for relieving gastrointestinal spasms by administering to a patient suffering from said gastrointestinal spasms a therapeutically effect amount between 0.5 mg. and 500 mg. per dosage unit of at least one of said compounds.

The compounds of structure I are also useful for relieving gastrointestinal hyperacidity or ulceration by administering to a patient suffering from said gastrointestinal hyperacidity or ulceration a therapeutically effective amount between 0.5 mg. and 500 mg. per dosage unit of at least one of said compounds.

The compound of structure I are also useful for relieving hypertensive disorders by administering to a patient suffering from said hypertensive disorders a therapeutically effect amount between 0.5 mg. to 500 mg. per dosage unit of at least one of said compounds.

The compounds of this invention may be prepared by the following general synthesis:

Condensation of a substitutedphenyl isocyanate (prepared from an aniline and phosgene in the customary manner) with guanidine results in a 1-substitutedphenyl-3-amidinourea. The reaction is carried out in a polar media using solvents such as alcohol, tetrahydrofuran, etc. It is convenient to carry out the reaction by preparing the isocyanate in the reaction media and then forming guanidine in situ by hydrolyzing guanidine carbonate with base condensation of the isocyanate takes place when the guanidine forms and the amidinourea compound results.

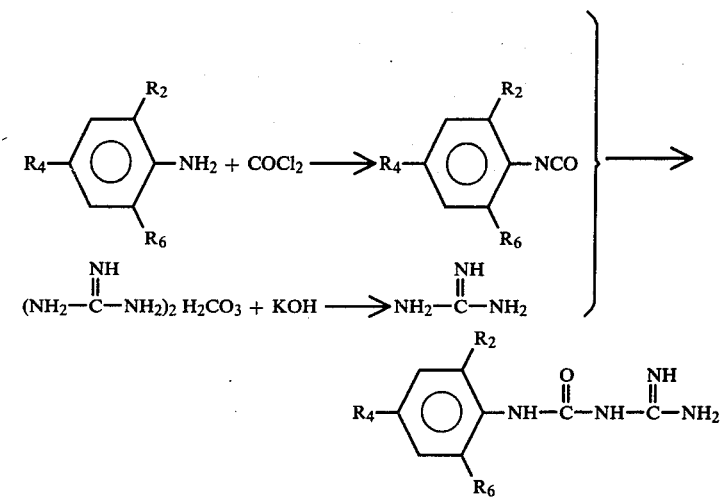

These compounds may also be prepared by degradation of the corresponding biguanide. When a 1-substitutedphenylbiguanide compound is hydrolyzed in acid at raised temperature then the resultant product is 1-substitutedphenyl-3-amidinourea. This reaction is preferably carried out using hydrochloric acid and the reaction time and reaction temperature will of course depend on the particular biguanide used and the concentration of the acid present. In general, the more concentrated acids will not require high temperatures of long periods of reation time.

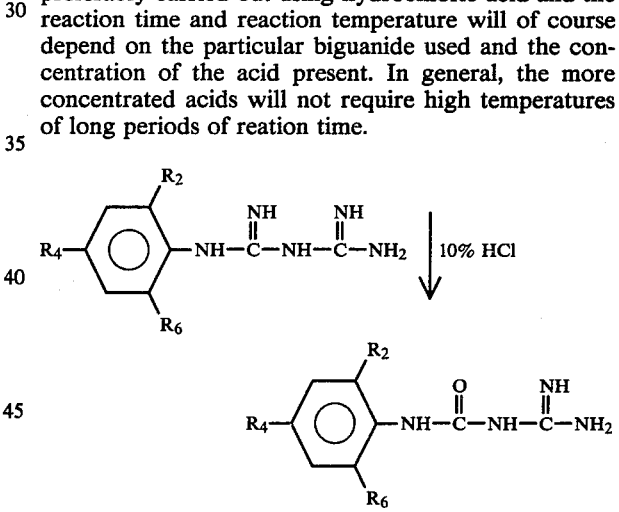

When it is desired to have R substitution the starting material of course will be an aniline having N-alkyl substitution. Reaction with phosgene results in the aniline acid chloride which is then reacted with the guanidine to prepare the amidinourea.

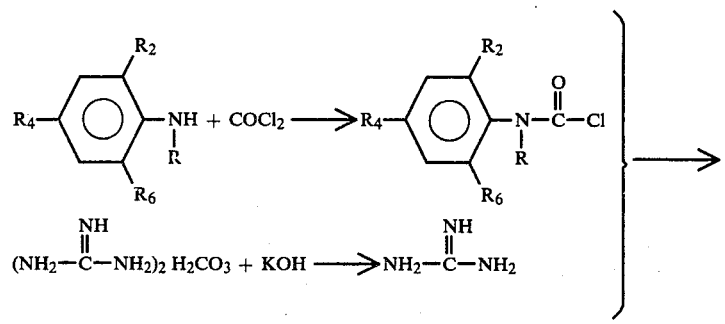

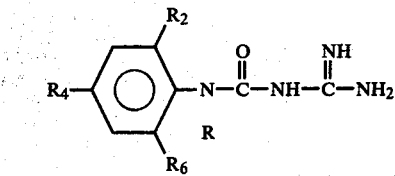

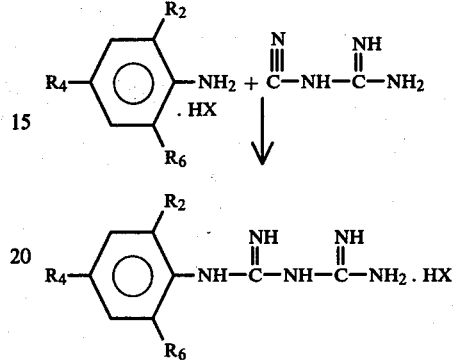

The starting anilines are either known, may be prepared by known techniques or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (Cl I).

Alkylation may be carried out on an acetanilide using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound. Diazotization followed by a Sandmeyer type reaction may yield the bromo, chloro or iodo compound.

When an amino compound is diazotized followed by reaction with potassium ethylxanthate and then hydrolyzed, the mercapto compound results. This in turn may be alkylated to the alkylthio group which is then oxidized to the corresponding alkylsulfonyl substituent.

A chloro, bromo or iodo compound may also be reacted with trifluoromethyliodide and copper powder at about 150° C. in dimethylformamide to obtain a trifluoromethyl compound [Tetrahedron Letters:47, 4095 (1959)].

A halo compound may also be reacted with cuprous methanesulfinate in quinoline at about 150° C. to obtain a methylsulfonyl compound.

Reactions may also be carried out at other stages of synthesis depending on the substituents present and the substituents desired and various combinations of the foregoing reactions will be determined by one skilled in the art in order that the desired product results. Thus, a phenylamidinourea may be halogenated or nitrated as above, etc.

The biguanide starting materials are also either known, may be prepared by known procedures or may be prepared by the following general synthesis:

Condensation of cyanoguanide and an aniline in the presence of an equimolar amount of a mineral acid results in the corresponding phenylbiguanide This reaction is preferably carried out on the aniline salt either in a polar media or neat and using increased temperatures. The appropriately substituted product may be prepared by the reactions above when these are also carried out on the biguanide.

The following are detailed examples which show the properties of the compounds of this invention. They are to be construed as illustrations of said compounds and not as limitations thereof.

EXAMPLE 1

1-Amidino-3-(2,6-dimethyl-4-chlorophenyl)urea

To 15.5 g (0.1 mole) of 2,6-dimethyl-4-chloroaniline in 300 ml of anhydrous benzene is added 325 ml of 12.5% phosgene in benzene (0.395 mole). The reaction mixture is refluxed for 2 hours and the benzene is stripped off under reduced pressure to get rid of the phosgene and the residing purified by distillation. This is then dissolved in 50 ml of tetrahydrofuran and added dropwise to a heterogeneous mixture of 11.2 g of potassium hydroxide and 18 g of guanidine carbonate in 250 ml tetrahydrofuran. This mixture is stirred for 8 hours and then 35 ml of conc. hydrochloric acid is added followed by 40 ml of conc. sodium hydroxide solution maintaining the mixture cool in a cold water bath. The mixture is next poured in 1500 ml of water and the tetrahydrofuran is removed under diminished pressure. The mixture is extracted with ether which is then dried and evaporated to dryness to obtain 1-amidino-3-(2,6-dimethyl-4-chlorophenyl)urea.

The hydrochloride solvent is prepared by dissolving the free base in methanol and adding a methanolic hydrogen chloride solution to form the salt. The volume of the mixture is concentrated, ether added and 1-amidino-3-(2,6-dimethyl-4-chlorophenyl)urea hydrochloride is filtered off.

When 2,6-dimethyl-4-chloroaniline in the above procedure is replaced by the aniline of Table I, below, then the corresponding products of Table II, below, are prepared.

TABLE I

| | |
|---|---|
| 2,4-dimethylaniline | 2,4,6-trimethylaniline |
| 2,4-diethylaniline | 2,4-dimethyl-6-ethylaniline |

TABLE I-continued

| | |
|---|---|
| 2-methyl-4-ethylaniline | 2,4-dimethyl-6-chloroaniline |
| 2-ethyl-4-methylaniline | 2,4-dimethyl-6-bromoaniline |
| 2,4-dipropylaniline | 2,4-dimethyl-6-fluoroaniline |
| 2-methyl-4-propylaniline | 2,4-dimethyl-6-trifluoromethylaniline |
| 2-ethyl-4-propylaniline | 2,4-dimethyl-6-nitroaniline |
| 2-propyl-4-methylaniline | 2,4-dimethyl-6-methylsulfonylaniline |
| 2-propyl-4-ethylaniline | 2,4-dimethyl-6-methoxyaniline |
| 2-methyl-4-butylaniline | 2,6-dimethyl-4-ethylaniline |
| 2-ethyl-4-butylaniline | 2,6-dimethyl-4-chloroaniline |
| 2-methyl-4-pentylaniline | 2,6-dimethyl-4-bromoaniline |
| 2-ethyl-4-pentylaniline | 2,6-dimethyl-4-fluoroaniline |
| 2-methyl-4-hexylaniline | 2,6-dimethyl-4-methoxyaniline |
| 2-ethyl-4-hexylaniline | 2-methyl-4,6-dichloroaniline |
| 2-methyl-4-heptylaniline | 2-methyl-4,6-difluoroaniline |
| 2-methyl-4-chloroaniline | 2-methyl-4-fluoro-6-chloroaniline |
| 2-methyl-4-bromoaniline | 2-methyl-4-chloro-6-fluoroaniline |
| 2-methyl-4-iodoaniline | 2-methyl-4-methoxy-6-chloroaniline |
| 2-methyl-4-fluoroaniline | 2-methyl-4-ethyl-6-chloroaniline |
| 2-ethyl-4-chloroaniline | 2-methyl-4-chloro-6-trifluoromethylaniline |
| 2-ethyl-4-bromoaniline | 2-ethyl-4,6-dichloroaniline |
| 2-ethyl-4-fluoroaniline | 2-ethyl-4,6-difluoroaniline |
| 2-propyl-4-chloroaniline | 2-ethyl-4-fluoro-6-chloroaniline |
| 2-propyl-4-fluoroaniline | 2-ethyl-4-chloro-6-fluoroaniline |
| 2,4-diethyl-6-chloroaniline | 2,6-diethyl-4-chloroaniline |
| 2,4-diethyl-6-bromoaniline | 2,6-diethyl-4-bromoaniline |
| 2,4-diethyl-6-fluoroaniline | 2,6-diethyl-4-fluoroaniline |
| 2,4-diethyl-6-methylaniline | 2,4-dimethyl-6-nitroaniline |
| 2,4,6-triethylaniline | 2,6-diethyl-4-methylaniline |

TABLE II 1-amidino-3-(2,4-dimethylphenyl)urea
1-amidino-3-(2,4-diethylphenyl)urea
1-amidino-3-(2-methyl-4-ethylphenyl)urea
1-amidino-3-(2-ethyl-4-methylphenyl)urea
1-amidino-3-(2,4-dipropylphenyl)urea
1-amidino-3-(2-methyl-4-propylphenyl)urea
1-amidino-3-(2-ethyl-4-propylphenyl)urea
1-amidino-3-(2-propyl-4-methylphenyl)urea
1-amidino-3-(2-propyl-4-ethylphenyl)urea
1-amidino-3-(2-methyl-4-butylphenyl)urea
1-amidino-3-(2-ethyl-4-butylphenyl)urea
1-amidino-3-(2-methyl-4-pentylphenyl)urea
1-amidino-3-(2-ethyl-4-pentylphenyl)urea
1-amidino-3-(2-methyl-4-hexylphenyl)urea
1-amidino-3-(2-ethyl-4-hexylphenyl)urea
1-amidino-3-(2-methyl-4-heptylphenyl)urea
1-amidino-3-(2-methyl-4-chlorophenyl)urea
1-amidino-3-(2-methyl-4-bromophenyl)urea
1-amidino-3-(2-methyl-4-iodophenyl)urea
1-amidino-3-(2-methyl-4-fluorophenyl)urea
1-amidino-3-(2-ethyl-4-chlorophenyl)urea
1-amidino-3-(2-ethyl-4-bromophenyl)urea
1-amidino-3-(2-ethyl-4-fluorophenyl)urea
1-amidino-3-(2-propyl-4-chlorophenyl)urea
1-amidino-3-(2-propyl-4-fluorophenyl)urea
1-amidino-3-(2,4-diethyl-6-chlorophenyl)urea
1-amidino-3-(2,4-diethyl-6-bromophenyl)urea
1-amidino-3-(2,4-diethyl-6-fluorophenyl)urea
1-amidino-3-(2,4-diethyl-6-methylphenyl)urea
1-amidino-3-(2,4,6-triethylphenyl)urea
1-amidino-3-(2,4,6-trimethylphenyl)urea
1-amidino-3-(2,4-dimethyl-6-ethylphenyl)urea
1-amidino-3-(2,4-dimethyl-6-chlorophenyl)urea
1-amidino-3-(2,4-dimethyl-6-bromophenyl)urea

TABLE II-continued 1-amidino-3-(2,4-dimethyl-6-fluorophenyl)urea
1-amidino-3-(2,4-dimethyl-6-trifluoromethylphenyl)urea
1-amidino-3-(2,4-dimethyl-6-nitrophenyl)urea
1-amidino-3-(2,4-dimethyl-6-methylsulfonylphenyl)urea
1-amidino-3-(2,4-dimethyl-6-methoxyphenyl)urea
1-amidino-3-(2,6-dimethyl-4-ethylphenyl)urea
1-amidino-3-(2,6-dimethyl-4-chlorophenyl)urea
1-amidino-3-(2,6-dimethyl-4-bromophenyl)urea
1-amidino-3-(2,6-dimethyl-4-fluorophenyl)urea
1-amidino-3-(2,6-dimethyl-4-methoxyphenyl)urea
1-amidino-3-(2-methyl-4,6-dichlorophenyl)urea
1-amidino-3-(2-methyl-4,6-difluorophenyl)urea
1-amidino-3-(2-methyl-4-fluoro-6-chlorophenyl)urea
1-amidino-3-(2-methyl-4-chloro-6-fluorophenyl)urea
1-amidino-3-(2-methyl-4-methoxy-6-chlorophenyl)urea
1-amidino-3-(2-methyl-4-ethyl-6-chlorophenyl)urea
1-amidino-3-(2-methyl-4-chloro-6-trifluoromethylphenyl)urea
1-amidino-3-(2-ethyl-4,6-dichlorophenyl)urea
1-amidino-3-(2-ethyl-4,6-difluorophenyl)urea
1-amidino-3-(2-ethyl-4-fluoro-6-chlorophenyl)urea
1-amidino-3-(2-ethyl-4-chloro-6-fluorophenyl)urea
1-amidino-3-(2,6-diethyl-4-chlorophenyl)urea
1-amidino-3-(2,6-diethyl-4-bromophenyl)urea
1-amidino-3-(2,6-diethyl-4-fluorophenyl)urea
1-amidino-3-(2,4-dimethyl-6-nitrophenyl)urea
1-amidino-3-(2,6-diethyl-4-methylphenyl)urea

EXAMPLE 2

1-Amidino-3-(2-methyl-4,6-dichlorophenyl)-3-methylurea

To 19.0 (0.1 mole) of 2,4-dichloro-6,N-dimethylaniline in 300 ml of anhydrous benzene is added 325 ml of 12.5% phosgene in benzene (0.40 mole). The reaction mixture is refluxed for 2 hours and the benzene removed under reduced pressure to also eliminate any excess phosgene. The residue is 2,4-dichloro-6,N-dimethylaniline acid chloride. This is then dissolved in 50 ml of tetrahydrofuran and added dropwise to a heterogeneous mixture of 11.2 g of potassium hydroxide and 18 g of guanidine carbonate in 250 ml of tetrahydorfuran. The mixture is stirred for about 10 hours, acidified with conc. hydrochloric acid and then bacified with conc. sodium hydroxide solution while maintaining the mixture in an HCl bath. This is then poured into 1500 ml of water and the THF removed under diminished pressure. The mixture is extracted with ether, which is then dried and evaporated to dryness to obtain 1-amidino-3-(2-methyl-4,6-dichlorophenyl)-3-methylurea.

The hydrochloride salt is prepared by dissolving the free base in methanol and adding methanolic HCl to form the salt. The addition of ether accelerates the precipitation of the salt which is filtered off to obtain 1-amidino-3-(2-methyl-4,6-dichlorophenyl)-3-methylurea hydrochloride.

When 2,4-dichloro-6,N-dimethylaniline in the above example is replaced by the anilines of Table I, below, then the corresponding products of Table II, below, are prepared.

TABLE I

| | |
|---|---|
| N-methyl-2,4-dimethylaniline | N-methyl-2,4,6-trimethylaniline |
| N-methyl-2,4-diethylaniline | N-methyl-2,4-dimethyl-6-ethylaniline |
| N-methyl-2-methyl-4-ethylaniline | N-methyl-2,4-dimethyl-6-chloroaniline |
| N-methyl-2-ethyl-4-methylaniline | N-methyl-2,4-dimethyl-6-bromoaniline |
| N-methyl-2,4-dipropylaniline | N-methyl-2,4-dimethyl-6-fluoroanile |
| N-methyl-2-methyl-4-propylaniline | N-methyl-2,4-dimethyl-6-trifluoromethylaniline |
| N-methyl-2-ethyl-4-propylaniline | N-methyl-2,4-dimethyl-6-nitroaniline |
| N-methyl-2-propyl-4-methylaniline | N-methyl-2,4-dimethyl-6-methylsulfonylaniline |
| N-methyl-2-propyl-4-ethylaniline | N-methyl-2,4-dimethyl-6-methoxyaniline |
| N-methyl-2-methyl-4-butylaniline | N-methyl-2,6-dimethyl-4-ethylaniline |
| N-methyl-2-ethyl-4-butylaniline | N-methyl-2,6-dimethyl-4-chloroaniline |

TABLE I-continued

N-methyl-2-methyl-4-pentylaniline
N-methyl-2-ethyl-4-pentylaniline
N-methyl-2-methyl-4-hexylaniline
N-methyl-2-ethyl-4-hexylaniline
N-methyl-2-methyl-4-heptylaniline
N-methyl-2-methyl-4-chloroaniline
N-methyl-2-methyl-4-bromoaniline
N-methyl-2-methyl-4-iodoaniline
N-methyl-2-methyl-4-fluoroaniline N-methyl-2-ethyl-4-chloroaniline
N-methyl-2-ethyl-4-bromoaniline
N-methyl-2-ethyl-4-fluoroniline
N-methyl-2-propyl-4-chloroaniline
N-methyl-2-propyl-4-fluoroaniline
N-methyl-2-methyl-4-methoxyaniline
N-methyl-2-methyl-4-ethoxyaniline
N-methyl-2-ethyl-4-methoxyaniline
N-methyl-2-ethyl-4-ethoxyaniline
N-methyl-2-methyl-4-propoxyaniline
N-ethyl-2-methyl-4-ethylaniline N-ethyl-2-ethyl-4-methylaniline
N-ethyl-2-methyl-4-chloroaniline
N-ethyl-2-methyl-4-bromoaniline
N-ethyl-2-methyl-4-iodoaniline
N-ethyl-2-methyl-4-fluoroaniline
N-ethyl-2-ethyl-4-chloroaniline
N-ethyl-2-ethyl-4-bromoaniline
N-ethyl-2-ethyl-4-fluoroaniline
N-ethyl-2-propyl-4-chloroaniline
N-ethyl-2-propyl-4-fluoroaniline
N-ethyl-2-methyl-4-methoxyaniline
N-ethyl-2-methyl-4-ethoxyaniline
N-ethyl-2-ethyl-4-methoxyaniline
N-ethyl-4-ethoxyaniline
N-ethyl-2-methyl-4-propoxyaniline
N-ethyl-2,4-trimethylaniline
N-ethyl-2,4-dimethyl-6-ethylaniline
N-ethyl-2,4-dimethyl-6-chloroaniline
N-ethyl-2,4-dimethyl-6-fluoroaniline
N-ethyl-2,4-dimethyl-6-nitroaniline
N-ethyl-2,6-dimethyl-4-ethylaniline
N-ethyl-2,6-dimethyl-4-chloroaniline
N-ethyl-2,6-dimethyl-4-bromoaniline
N-ethyl-2,6-dimethyl-4-fluoroaniline
N-ethyl-2,6-dimethyl-4-methoxyaniline
N-ethyl-2-methyl-4,6-dichloroaniline
N-ethyl-2-methyl-4,6-difluoroaniline
N-ethyl-2-methyl-4-fluoro-6-chloroaniline
N-ethyl-2-methyl-4-chloro-6-fluoroaniline
N-ethyl-2-methyl-4-methoxy-6-chloroaniline
N-ethyl-2-methyl-4-ethyl-6-chloroaniline N-methyl-2,6-dimethyl-4-bromoaniline
N-methyl-2,6-dimethyl-4-fluoroaniline
N-methyl-2,6-dimethyl-4-methoxyaniline
N-methyl-2-methyl-4,6-difluoroaniline
N-methyl-2-methyl-4-fluoro-6-chloroaniline
N-methyl-2-methyl-4-chloro-6-fluoroaniline
N-methyl-2-methyl-4-methoxy-6-chloroaniline
N-methyl-2-methyl-4-ethyl-6-chloroaniline
N-methyl-2-methyl-4-chloro-6-trifluoro-Methylaniline
N-methyl-2-ethyl-4,6-dichloroaniline
N-methyl-2-ethyl-4,6-difluoroaniline
N-methyl-2-ethyl-4-fluoro-6-chloroaniline
N-methyl-2-ethyl-4-chloro-6-fluoroaniline
N-methyl-2,6-diethyl-4-chloroaniline
N-methyl-2,6-diethyl-4-bromoaniline
N-methyl-2,6-diethyl-4-fluoraniline
N-methyl-2,4-dimethyl-6-nitroaniline
N-ethyl-2,4-dimethylaniline
N-ethyl-2,4-diethylaniline
N-ethyl-2-methyl-4-chloro-6-trifluro-methylaniline
N-propyl-2,4-dimethylaniline
N-propyl-2-methyl-4-chloroaniline
N-propyl-2-methyl-4-fluoroaniline
N-propyl-2,6-dimethyl-4-chloroaniline
N-propyl-2,6-dimethyl-4-fluoroaniline
N-propyl-2,4-dimethyl-6-chloroaniline
N-propyl-2,4-dimethyl-6-fluoroaniline
N-butyl-2,4-dimethylaniline
N-butyl-2-methyl-4-chloroaniline
N-butyl-2-methyl-4-fluoroaniline

TABLE II 1-amidino-3-(2,4-dimethylphenyl)-3-methylurea
1-amidino-3-(2,4-diethylphenyl)-3-methylurea
1-amidino-3-(2-methyl-4-ethylphenyl)-3-methylurea
1-amidino-3-(2-ethyl-4-methylphenyl)-3-methylurea
1-amidino-3-(2,4-dipropylphenyl)-3-methylurea
1-amidino-3-(2-methyl-4-propylphenyl)-3-methylurea
1-amidino-3-(2-ethyl-4-propylphenyl)-3-methylurea
1-amidino-3-(2-propyl-4-methylphenyl)-3-methylurea
1-amidino-3-(2-propyl-4-ethylphenyl)-3-methylurea
1-amidino-3-(2-methyl-4-butylphenyl)-3-methylurea
1-amidino-3-(2-ethyl-4-butylphenyl)-3-methylurea
1-amidino-3-(2-methyl-4-pentylphenyl)-3-methylurea
1-amidino-3-(2-ethyl-4-pentylpheny)-3-methylurea
1-amidino-3-(2-methyl-4-hexylphenyl)-3-methylurea
1-amidino-3-(2-ethyl-4-hexylphenyl)-3-methylurea
1-amidino-3-(2-methyl-4-heptylphenyl)-3-methylurea
1-amidino-3-(2-methyl-4-chlorophenyl)-3-methylurea
1-amidino-3-(2-methyl-4-bromophenyl)-3-methylurea
1-amidino-3-(2-iodophenyl)-3-methylurea
1-amidino-3-(2-methyl-4-fluorphenyl)-3-methylurea
1-amidino-3-(2-ethyl-4-chlorophenyl)-3-methylurea
1-amidino-3-(2-ethyl-4-bromophenyl)-3-methylurea
1-amidino-3-(2-ethyl-4-fluorophenyl)-3-methylurea
1-amidino-3-(2-propyl-4-chlorophenyl)-3-methylurea
1-amidino-3-(2-propyl-4-fluorophenyl)-3-methylurea
1-amidino-3-(2-methyl-4-methoxyphenyl)-3-methylurea
1-amidino-3-(2-methyl-4-ethoxyphenyl)-3-methylurea
1-amidino-3-(2-ethyl-4-methoxyphenyl)-3-methylurea
1-amidino-3-(2-ethyl-4-ethoxyphenyl)-3-methylurea
1-amindino-3-(2-ethyl-4-methoxyphenyl)-3-methylurea
1-amidino-3-(2-methyl-4-propoxyphenyl)-3-methylurea
1-amidino-3-(2,4,6-trimethylphenyl)-3-methylurea
1-amidino-3-(2,4-dimethyl-6-ethylphenyl)-3-methylurea
1-amidino-3-(2,4-dimethyl-6-chlorophenyl)-3-methylurea
1-amidino-3-(2,4-dimethyl-6-bromophenyl)-3-methylurea
1-amidino-3-(2,4-dimethyl-6-fluorophenyl)-3-methylurea
1-amidino-3-(2,4-dimethyl-6-trifluoromethylphenyl)-3-methylurea
1-amidino-3-(2,4-dimethyl-6-nitrophenyl)-3-methylurea
1-amidino-3-(2,4-dimethyl-6-methylsulfonylphenyl)-3-methylurea
1-amidino-3-(2,4-dimethyl-6-methoxyphenyl)-3-methylurea
1-amidino-3-(2,6-dimethyl-4-ethylphenyl)-3-methylurea
1-amidino-3-(2,6-dimethyl-4-chlorophenyl)-3-methylurea
1-amidino-3-(2,6-dimethyl-4-bromophenyl)-3-methylurea
1-amidino-3-(2,6-dimethyl-4-fluorophenyl)-3-methylurea
1-amidino-3-(2,6-dimethyl-4-methoxyphenyl)-3-methylurea
1-amidino-3-(2-methyl-4,6-difluorophenyl)-3-methylurea

TABLE II-continued 1-amidino-3-(2-methyl-4-fluoro-6-chlorophenyl)-3-methylurea
1-amidino-3-(2-methyl-4-chloro-6-fluorophenyl)-3-methylurea
1-amidino-3-(2-methyl-4-methoxy-6-chlorophenyl)-3-methylurea
1-amidino-3-(2-methyl-4-ethyl-6-chlorophenyl)-3-methylurea
1-amidino-3-(2-methyl-4-chloro-6-trifluoromethylphenyl)-3-methylurea
1-amidino-3-(2-ethyl-4,6-dichlorophenyl)-3-methylurea
1-amidino-3-(2-ethyl-4,6-difluorophenyl)-3-methylurea
1-amidino-3-(2-ethyl-4-fluoro-6-chlorophenyl)-3-methylurea
1-amidino-3-(2-ethyl-4-chloro-6-fluorophenyl)-3-methylurea
1-amidino-3-(2,6-diethyl-4-chlorophenyl)-3-methylurea
1-amidino-3-(2,6-diethyl-4-bromophenyl)-3-methylurea
1-amidino-3-(2,6-diethyl-4-fluorophenyl)-3-methylurea
1-amidino-3-(2,4-dimethyl-6-nitrophenyl)-3-methylurea
1-amidino-3-(2,4-dimethylphenyl)-3-methylurea
1-amidino-3-(2,4-diethylphenyl)-3-methylurea
1-amidino-3-(2-methyl-4-ethylphenyl)-3-ethylurea
1-amidino-3-(2-ethyl-4-methylphenyl)-3-ethylurea
1-amidino-3-(2-methyl-4-chlorophenyl)-3-ethylurea
1-amidino-3-(2-methyl-4-bromophenyl)-3-ethylurea
1-amidino-3-(2-methyl-4-bromophenyl)-3-ethylurea
1-amidino-3-(2-methyl-4-iodophenyl)-3-ethylurea
1-amidino-3-(2-methyl-4-fluorophenyl)-3-ethylurea
1-amidino-3-(2-ethyl-4-chlorophenyl)-3-ethylurea
1-amidino-3-(2-ethyl-4-bromophenyl)-3-ethylurea
1-amidino-3-(2-ethyl-4-fluorophenyl)-3-ethylurea
1-amidino-3-(2-propyl-4-chlorophenyl)-3-ethylurea
1-amidino-3-(2-propyl-4-fluorophenyl)-3-ethylurea
1-amidino-3-(2-propyl-4-methoxyphenyl)-3-ethylurea
1-amidino-3-(2-methyl-4-ethoxyphenyl)-3-ethylurea
1-amidino-3-(2-ethyl-4-methoxyphenyl)-3-ethylurea
1-amidino-3-(2-ethyl-4-ethoxyphenyl)-3-ethylurea
1-amidino-3-(2-methyy-4-propoxyphenyl)-3-ethylurea
1-amidino-3-(2,4-trimethylphenyl)-3-ethylurea
1-amidino-3-(2,4-dimethyl-6-ethylphenyl)-3-ethylurea
1-amidino-3-(2,4-dimethyl-6-chlorophenyl)-3-ethylurea
1-amidino-3-(2,4-dimethyl-6-fluorophenyl)-3-ethylurea
1-amidino-3-(2,4-dimethyl-6-nitrophenyl)-3-ethylurea
1-amidino-3-(2,6-dimethyl-4-ethylphenyl)-3-ethylurea
1-amidino-3-(2,6-dimethyl-4-chlorophenyl)-3-ethlurea
1-amidino-3-(2,6-dimethyl-4-bromophenyl)-3-ethylurea
1-amidino-3-(2,6-dimethyl-4-fluorophenyl)-3-ethylurea
1-amidino-3-(2,6-dimethyl-4-methoxyphenyl)-3-ethylurea
1-amidino-3-(2-methyl-4,6-dichlorophenyl)-3-ethylurea
1-amidino-3-(2-methyl-4,6-difluorophenyl)-3-ethylurea
1-amidino-3-(2-methyl-4-fluoro-6-chlorophenyl)-3-ethylurea
1-amidino-3-(2-methyl-4-chloro-6-fluorophenyl)-3-ethylurea
1-amidino-3-(2-methyl-4-methoxy-6-chlorophenyl)-3-ethylurea
1-amidino-3-(2-methyl-4-ethyl-6-chlorophenyl)-3-ethylurea
1-amidino-3-(2-methyl-4-chloro-6-trifluoromethylphenyl)-3-ethylurea
1-amidino-3-(2,4-dimethylphenyl)-3-propylurea
1-amidino-3-(2-methyl-4-chlorophenyl)-3-propylurea
1-amidino-3-(2-methyl-4-fluorophenyl)-3-propylurea
1-amidino-3-(2,6-dimethyl-4-chlorophenyl)-3-propylurea
1-amidino-3-(2,6-dimethyl-4-fluorophenyl)-3-propylurea
1-amidino-3-(2,4-dimethyl-6-chlorophenyl)-3-propylurea
1-amidino-3-(2,4-dimethyl-6-fluorophenyl)-3-propylurea
1-amidino-3-(2,4-dimethylphenyl)-3-butylurea
1-amidino-3-(2-methyl-4-chlorophenyl)-3-butylurea
1-amidino-3-(2-methy1-4-fluorophenyl)-3-butylurea

EXAMPLE 3

1-Amidino-3-(2-methyl-4,6-dichlorophenyl)urea

A quantity of 20 g of (1-(2-methyl-4,6-dichlorophenyl)biguanide is added to 200 ml of 10% hydrochloric acid and the mixture is refluxed for 3 hours. The reaction mixture is then filtered hot and then chilled. The material which separates is then filtered off and recrystallized from isopropanol/water to obtain 1-amidino-3-(2-methyl-4,6-dichlorophenyl)urea hydrochloride.

The free base is prepared by dissolving the salt in 200 ml of water and adding a 10% sodium hydroxide solution until alkaline. The reaction mixture is then extracted with chloroform which is dried and evaporated to dryness to obtain 1-amidino-3-(2-methyl-4,6-dichlorophenyl)urea.

When the biguanides of Table I, below, are used in the above example in place of 1-(2-methyl-4,6-dichlorophenyl)biguanide then the corresponding products of Table II are prepared.

TABLE I 1-(2,4-dimethylphenyl)biguanide
1-(2,4-diethylpheneyl)biguanide
1-(2-methyl-4-ethylphenyl)biguanide
1-(2-ethyl-4-methylphenyl)biguanide
1-(2-methyl-4-chlorophenyl)biguanide
1-(2-methyl-4-bromophenyl)biguanide
1-(2-methyl-4-iodophenyl)biguanide
1-(2-methyl-4-fluorophenyl)biguanide
1-(2-ethyl-4-chlorophenyl)biguanide
1-(2-ethyl-4-fluorophenyl)biguanide
1-(2-methyl-4-methoxyphenyl)biguanide
1-(2-methyl-4-ethoxyphenyl)biguanide
1-(2,4,6-trimethylphenyl)biguanide
1-(2,4-dimethyl-6-ethylphenyl)biguanide
1-(2,4-dimethyl-6-chlorophenyl)biguanide
1-(2,4-dimethyl-6-fluorophenyl)biguanide
1-(2,4-dimethyl-6-trifluoromethylphenyl)biguanide
1-(2,4-dimethyl-6-nitrophenyl)biguanide
1-(2,6-dimethyl-4-chlorophenyl)biguanide
1-(2,6-dimethyl-4-fluorophenyl)biguanide
1-(2-methyl-4,6-dichlorophenyl)biguanide
1-(2-methyl-4,6-difluorophenyl)biguanide
1-(2-methyl-4-ethyl-6-chlorophenyl)biguanide
1-(2-ethyl-4,6-dichlorophenyl)biguanide
1-(2-ethyl-4,6-difluorophenyl)biguanide
1-(2,6-diethyl-4-chlorophenyl)biguanide
1-(2,6-diethyl-4-fluorophenyl)biguanide
1-methyl-1-(2,4-dimethylphenyl)biguanide
1-methyl-1-(2,4-diethylphenyl)biguanide
1-methyl-1-(2-methyl-4-ethylphenyl)biguanide
1-methyl-1-(2-ethyl-4-methylphenyl)biguanide
1-methyl-1-(2,4-diethyl-6-chlorophenyl)biguanide
1-methyl-1-(2,4-diethyl-6-methylphenyl)biguanide
1-methyl-1-(2-methyl-4-chlorophenyl)biguanide
1-methyl-1-(2-methyl-4-bromophenyl)biguanide
1-methyl-1-(2-methyl-4-fluorophenyl)biguanide
1-methyl-1-(2-ethyl-4-chlorophenyl)biguanide
1-methyl-1-(2-ethyl-4-fluorophenyl)biguanide
1-methyl-1-(2,4,6-trimethylphenyl)biguanide
1-methyl-1-(2,4-dimethyl-6-ethylphenyl)biguanide
1-methyl-1-(2,4-dimethyl-6-chlorophenyl)biguanide
1-methyl-1-(2,4-dimethyl-6-fluorophenyl)biguanide
1-methyl-1-(2,6-dimethyl-4-chlorophenyl)biguanide
1-methyl-1-(2,6-dimethyl-4-fluorophenyl)biguanide
1-methyl-1-(2-methyl-4,6-dichlorophenyl)biguanide
1-methyl-1-(2-ethyl-4,6-dichlorophenyl)biguanide
1-methyl-1-(2-methyl-4,6-difluorophenyl)biguanide
1-ethyl-1-(2,4-dimethylphenyl)biguanide
1-ethyl-1-(2,4-diethylphenyl)biguanide
1-ethyl-1-(2-methyl-4-ethylphenyl)biguanide
1-ethyl-1-(2-ethyl-4-methylphenyl)biguanide
1-ethyl-1-(2-methyl-4-chlorophenyl)biguanide
1-ethyl-1-(2-methyl-4-bromophenyl)biguanide
1-ethyl-1-(2-methyl-4-fluorophenyl)biguanide
1-ethyl-1-(2-ethyl-4-chlorophenyl)biguanide
1-ethyl-1-(2-ethyl-4-fluorophenyl)biguanide
1-ethyl-1-(2,4-dimethyl-6-fluorophenyl)biguanide
1-ethyl-1-(2,4-dimethyl-6-chlorophenyl)biguanide
1-ethyl-1-(2,4-dichloro-6-methylphenyl)biguanide
1-ethyl-1-(2,4-difluoro-6-methylphenyl)biguanide
1-propyl-1-(2,4-dimethylphenyl)biguanide
1-propyl-1-(2,4-diethylphenyl)biguanide
1-propyl-1-(2-methyl-4-chlorophenyl)biguanide
1-propyl-1-(2-methyl-4-bromophenyl)biguanide
1-propyl-1-(2-methyl-4-fluorophenyl)biguanide
1-propyl-1-(2-ethyl-4-chlorophenyl)biguanide
1-propyl-1-(2-ethyl-4-fluorophenyl)biguanide

TABLE II 1-amidino-3-(2,4-dimethylphenyl)urea
1-amidino-3-(2,4-diethylphenyl)urea
1-amidino-3-(2-methyl-4-ethylphenyl)urea
1-amidino-3-(2-ethyl-4-methylphenyl)urea
1-amidino-3-(2-methyl-4-chlorophenyl)urea

TABLE II-continued 1-amidino-3-(2-methyl-4-bromophenyl)urea
1-amidino-3-(2-methyl-4-iodophenyl)urea
1-amidino-3-(2-methyl-4-fluorophenyl)urea
1-amidino-3-(2-ethyl-4-chlorophenyl)urea
1-amidino-3-(2-ethyl-4-fluorophenyl)urea
1-amidino-3-(2-methyl-4-methoxyphenyl)urea
1-amidino-3-(2-methyl-4-ethoxyphenyl)urea
1-amidino-3-(2,4,6-trimethylphenyl)urea
1-amidino-3-(2,4-dimethyl-4-ethylphenyl)urea
1-amidino-3-(2,4-dimethyl-6-chlorophenyl)urea
1-amidino-3-(2,4-dimethyl-6-fluorophenyl)urea
1-amidino-3-(2,4-dimethyl-6-trifluoromethylphenyl)urea
1-amidino-3-(2,4-dimethyl-6-nitrophenyl)urea
1-amidino-3-(2,6-dimethyl-4-chlorophenyl)urea
1-amidino-3-(2,6-dimethyl-4-fluorophenyl)urea
1-amidino-3-(2-methyl-4,6-dichlorophenyl)urea
1-amidino-3-(2-methyl-4,6-difluorophenyl)urea
1-amidino-3-(2-methyl-4-ethyl-6-chlorophenyl)urea
1-amidino-3-(2-ethyl-4,6-dichlorophenyl)urea
1-amidino-3-(2-ethyl-4,6-difluorophenyl)urea
1-amidino-3-(2,6-diethyl-4-chlorophenyl)urea
1-amidino-3-(2,6-diethyl-4-fluorophenyl)urea
1-amidino-3-(2,4-diethyl-6-chlorophenyl)urea
1-amidino-3-(2,4-diethyl-6-methylphenyl)urea
3-methyl-1-(2,4-dimethylphenyl)urea
3-methyl-1-(2,4-diethylphenyl)urea
3-methyl-1-(2-methyl-4-ethylphenyl)urea
3-methyl-1-(2-ethyl-4-methylphenyl)urea
3-methyl-1-(2-methyl-4-chlorophenyl)urea
3-methyl-1-(2-methyl-4-bromophenyl)urea
3-methyl-1-(2-methyl-4-fluorophenyl)urea
3-methyl-1-(2-ethyl-4-chlorophenyl)urea
3-methyl-1-(2-ethyl-4-fluorophenyl)urea
3-methyl-1-(2,4,6-trimethylphenyl)urea
3-methyl-1-(2,4-dimethyl-6-ethylphenyl)urea
3-methyl-1-(2,4-dimethyl-6-chlorophenyl)urea
3-methyl-1-(2,4-dimethyl-6-fluorophenyl)urea
3-methyl-1-(2,6-dimethyl-4-chlorophenyl)urea
3-methyl-1-(2,6-dimethyl-4-fluorophenyl)urea
3-methyl-1-(2-methyl-4,6-dichlorophenyl)urea
3-methyl-1-(2-ethyl-4,6-dichlorophenyl)urea
3-methyl-1-(2-methyl-4,6-difluorophenyl)urea
3-ethyl-1-(2,4-dimethylphenyl)urea
3-ethyl-1-(2,4-diethylphenyl)urea
3-ethyl-1-(2-methyl-4-ethylphenyl)urea
3-ethyl-1-(2-ethyl-4-methylphenyl)urea
3-ethyl-1-(2-methyl-4-chlorophenyl)urea
3-ethyl-1-(2-methyl-4-bromophenyl)urea
3-ethyl-1-(2-methyl-4-fluorophenyl)urea
3-ethyl-1-(2-ethyl-4-chlorophenyl)urea
3-ethyl-1-(2-ethyl-4-fluorophenyl)urea
3-ethyl-1-(2,4-dimethyl-6-fluorophenyl)urea
3-ethyl-1-(2,4-dimethyl-6-chlorophenyl)urea
3-ethyl-1-(2,4-dichloro-6-methylphenyl)urea
3-ethyl-1-(2,4-difluoro-6-methylphenyl)urea
3-propyl-1-(2,4-dimethylphenyl)urea
3-propyl-1-(2,4-diethylphenyl)urea
3-propyl-1-(2-methyl-4-chlorophenyl)urea
3-propyl-1-(2-methyl-4-bromophenyl)urea
3-propyl-1-(2-methyl-4-fluorophenyl)urea
3-propyl-1-(2-ethyl-4-chlorophenyl)urea
3-propyl-1-(2-ethyl-4-fluorophenyl)urea

We claim:
1. A compound of the formula

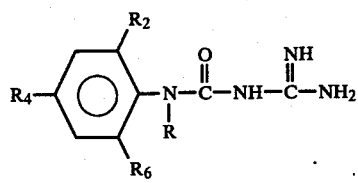

where:
R is hydrogen or loweralkyl;
$R_2$ is loweralkyl;
$R_4$ is loweralkyl, halo or loweralkoxy;
$R_6$ is hydrogen, loweralkyl, halo, haloloweralkyl, nitro, loweralkylsulfonyl or loweralkoxy; and
the non-toxic acid addition salts thereof.

2. A compound according to claim 1 where:
R is hydrogen or loweralkyl;
$R_2$ is loweralkyl;
$R_4$ is loweralkyl or halo; and
$R_6$ is loweralkyl or halo.

3. A compound according to claim 2 where:
R is hydrogen or methyl;
$R_2$ is methyl or ethyl;
$R_4$ is methyl, ethyl, propyl, i-propyl, butyl, chloro, bromo or fluoro; and
$R_6$ is methyl, ethyl, chloro, bromo or fluoro.

4. A compound according to claim 3 where:
R is hydrogen or methyl;
$R_2$ is methyl or ethyl;
$R_4$ is methyl, ethyl, chloro, bromo or fluoro; and
$R_6$ is methyl, ethyl, chloro or bromo.

5. A compound according to claim 4 wherein is hydrogen.

6. A compound according to claim 4 where R is methyl.

7. A compound according to claim 5 where $R_2$ and RHd 6 are methyl.

8. A compound according to claim 5 where $R_2$ is methyl and $R_6$ is ethyl.

9. A compound according to claim 5 where $R_2$ is methyl and $R_6$ is chloro.

10. A compound according to claim 5 where $R_2$ and $R_6$ are ethyl.

11. A compound according to claim 5 where $R_2$ is ethyl and $R_6$ is chloro.

12. A compound according to claim 5 where $R_2$ and $R_4$ are methyl.

13. A compound according to claim 5 where $R_2$ and $R_4$ are ethyl.

14. A compound according to claim 5 where $R_2$ is methyl and $R_4$ is ethyl.

15. A compound according to claim 5 where $R_2$ is methyl and $R_4$ is chloro.

16. A compound according to claim 5 where $R_2$ is ethyl and $R_4$ is chloro.

17. A compound according to claim 5 which is 1-amidino-3-(2,4,6-trimethylphenyl)urea.

18. A compound according to claim 5 which is 1-amidino-3-(2,4-dimethyl-6-chlorophenyl)urea.

19. A compound according to claim 5 which is 1-amidino-3-(2,4-dichloro-6-methylphenyl)urea.

20. A compound according to claim 5 which is 1-amidino-3-(2,6-dimethyl-4-chlorophenyl)urea.

21. A compound according to claim 5 which is 1-amidino-3-(2,6-dimethyl-4-ethylphenyl)urea.

22. A compound according to claim 5 which is 1-amidino-3-(2-methyl-4-chloro-6-ethylphenyl)urea.

23. A compound according to claim 5 which is 1-amidino-3-(2-methyl-4-ethyl-6-chlorophenyl)urea.

24. A compound according to claim 5 which is 1-amidino-3-(2,4,6-triethylphenyl)urea.

25. A compound according to claim 5 which is 1-amidino-3-(2,4-dimethylphenyl)urea.

26. A compound according to claim 5 which is 1-amidino-3-(2-methyl-4-chlorophenyl)urea.

27. A compound according to claim 5 which is 1-amidino-3-(2-methyl-4-bromophenyl)urea.

28. A compound according to claim 6 which is 1-amidino-3-methyl-3-(2,4-dimethyl-6-chlorophenyl)urea.

29. A compound according to claim 6 which is 1-amidino-3-methyl-3-(2,4-dichloro-6-methylphenyl)urea.

30. A compound according to claim 6 which is 1-amidino-3-methyl-3-(2,4,6-trimethylphenyl)urea.

31. A compound according to claim 6 which is 1-amidino-3-methyl-3-(2,6-dimethyl-4-chlorophenyl)urea.

32. A compound according to claim 6 which is 1-amidino-3-methyl-3-(2,4-dimethylphenyl)urea.

33. A compound according to claim 6 which is 1-amidino-3-methyl-3-(2-methyl-4-chlorophenyl)urea.

34. A method for relieving gastrointestinal spasms comprising administering to a patient suffering from said gastrointestinal spasms a therapeutically effective amount between 0.5 mg and 500 mg per dosage unit of at least one compound of the formula:

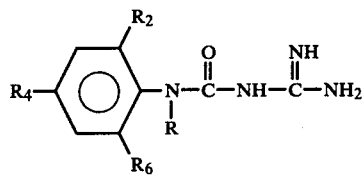

where:
R is hydrogen or loweralkyl;
$R_2$ is loweralkyl;
$R_4$ is loweralkyl, halo or loweralkoxy;
$R_6$ is hydrogen, loweralkyl, halo, haloloweralkyl, nitro, loweralkylsulfonyl or loweralkoxy; and
the non-toxic acid addition salts thereof.

35. A method according to claim 34 where:
R is hydrogen or loweralkyl;
$R_2$ is loweralkyl;
$R_4$ is loweralkyl or halo; and
$R_6$ is loweralkyl or halo.

36. A method according to claim 35 where:
R is hydrogen or methyl;
$R_2$ is methyl or ethyl;
$R_4$ is methyl, ethyl, propyl, i-propyl, butyl, chloro, bromo or fluoro; and
$R_6$ is methyl, ethyl, chloro, bromo or fluoro.

37. A method according to claim 36 where:
R is hydrogen or methyl;
$R_2$ is methyl or ethyl;
$R_4$ is methyl, ethyl, chloro, bromo or fluoro; and
$R_6$ is methyl, ethyl, chloro or bromo.

* * * * *